United States Patent
Uehara (10) Patent No.: US 10,772,598 B2
(45) Date of Patent: Sep. 15, 2020

(54) RADIATION CONTROL DEVICE

(71) Applicant: Konica Minolta, Inc., Tokyo (JP)

(72) Inventor: Takahisa Uehara, Kanagawa (JP)

(73) Assignee: KONICA MINOLTA, INC., Tokyo (JP)

( * ) Notice: Subject to any disclaimer, the term of this patent is extended or adjusted under 35 U.S.C. 154(b) by 0 days.

(21) Appl. No.: 16/124,905

(22) Filed: Sep. 7, 2018

(65) Prior Publication Data

US 2019/0076107 A1    Mar. 14, 2019

(30) Foreign Application Priority Data

Sep. 12, 2017    (JP) .................... 2017-174886

(51) Int. Cl.
*A61B 6/00*    (2006.01)

(52) U.S. Cl.
CPC ............ *A61B 6/54* (2013.01); *A61B 6/46* (2013.01); *A61B 6/56* (2013.01); *A61B 6/4233* (2013.01); *A61B 6/465* (2013.01); *A61B 6/548* (2013.01); *A61B 6/566* (2013.01)

(58) Field of Classification Search
CPC .... A61B 6/54; A61B 6/46; A61B 6/56; A61B 6/566; A61B 6/548; A61B 6/465; A61B 6/4233
See application file for complete search history.

(56) References Cited

U.S. PATENT DOCUMENTS

| | | | |
|---|---|---|---|
| 8,953,744 B2 * | 2/2015 | Watanabe | H04N 5/32 250/370.09 |
| 9,060,738 B2 * | 6/2015 | Kuwabara | A61B 6/548 |
| 9,453,923 B2 * | 9/2016 | Eguchi | A61B 6/4233 |
| 2013/0279657 A1 * | 10/2013 | Hiroike | A61B 6/4233 378/62 |
| 2014/0254760 A1 * | 9/2014 | Hiroike | A61B 6/4233 378/62 |
| 2016/0143602 A1 * | 5/2016 | Hiroike | A61B 6/463 378/98.5 |
| 2017/0303885 A1 * | 10/2017 | Hosoki | A61B 6/4064 |

FOREIGN PATENT DOCUMENTS

WO    2012/032800    3/2012

\* cited by examiner

*Primary Examiner* — Kiho Kim
(74) *Attorney, Agent, or Firm* — Lucas & Mercanti, LLP (57) ABSTRACT

A radiation control device includes a notifier that notifies an irradiation state of a radiation in a radiation generator, and a notification controller that controls notification operation of the notifier. The notification controller controls a start timing of notification of a state during irradiation indicating that the radiation is being emitted on the basis of a signal from the radiation generator or a radiation imager received by the radiation control device prior to a radiation irradiation signal from a radiation generation controller.

6 Claims, 5 Drawing Sheets

FIG. 4D

RADIATION CONTROL DEVICE

CROSS REFERENCE TO RELATED APPLICATIONS

Japanese Patent Application No. 2017-174886 filed on Sep. 12, 2017, including description, claims, drawings, and abstract the entire disclosure is incorporated herein by reference in its entirety.

BACKGROUND

Technological Field

The present invention relates to a radiation control device that controls a radiation imaging system in cooperation with a radiation generating control device.

Description of Related Art

Conventionally, diagnostic imaging using an X-ray imaging system has been performed in the medical field. In recent years, along with the development of a flat panel detector (FPD) that generates an X-ray image on the basis of an incident X-ray, a diagnosis technique using an X-ray dynamic imaging is also being established. According to the X-ray dynamic imaging, in addition to morphological information of a respiratory organ and a circulatory organ, dynamic information can be obtained from a change in a pixel value (density) of an X-ray image. For example, a lung ventilation function and a pulmonary blood flow with regard to a chest region can be dynamically diagnosed.

In general, an X-ray imaging system includes an X-ray generating device that generates an X-ray and irradiates a subject with the X-ray, and an X-ray imaging device that captures an X-ray image on the basis of an amount of the incident X-rays transmitted through the subject.

The X-ray generating device includes an X-ray tube device that irradiates the subject with the X-ray, a high voltage generating device that applies a voltage to the X-ray tube device, an X-ray generation control device that controls operation of the X-ray tube device and the high voltage generating device, an X-ray generation console for inputting and checking an irradiation condition and the like, and an irradiation switch that provides an instruction on an X-ray irradiation.

The X-ray imaging device includes an FPD that detects the X-ray transmitted through the subject, convers the detected X-ray into image data, and outputs the image data, an imaging control device that controls operation of the FPD and performs a predetermined processing (e.g., image processing and display control processing) on the obtained X-ray image data, and an imaging console for inputting and checking an imaging condition and the like. The captured X-ray image is displayed on the imaging console.

In the X-ray imaging system, it is stipulated that an X-ray irradiation state is displayed with light in a predetermined color (General Requirements for High-voltage Generators of Medical X-ray Apparatus: JIS Z 4702). In general, the X-ray generation console is provided with a display lamp including a light emitting element such as a light emitting diode (LED), and the X-ray irradiation state is notified by lighting/non-lighting of the display lamp. For example, the display lamp lights up in a green color in an X-ray irradiation preparation state, and lights up in an orange color in a state during X-ray irradiation.

When the X-ray irradiation state is displayed using the display lamp of the X-ray generation console, the operation of the display lamp is also controlled in accordance with an X-ray irradiation signal by which the X-ray generation control device instructs the high voltage generating device to emit the X-ray, whereby no delay is caused with respect to the lighting of the display lamp, and the X-ray irradiation state can be accurately notified.

Meanwhile, in recent years, an integrated X-ray imaging system in which a signal or the like is exchanged between the X-ray generating device and the X-ray imaging device and an X-ray imaging is performed while the two devices cooperate with each other has become a mainstream (see WO 2012/032800, for example). In the integrated X-ray imaging system, the X-ray generation console is omitted, and information associated with the X-ray generating device is input and displayed on the imaging console. In the integrated X-ray imaging system as well, as described above, the X-ray irradiation state is required to be displayed with the light in the predetermined color.

However, when a display control of the imaging console is performed in accordance with the X-ray irradiation signal from the X-ray generation control device, a delay corresponding to the time required for the signal transmission is caused. In addition, since a display of the imaging console is configured by a display device on which display control is performed by software processing such as a liquid crystal display and a cathode ray tube (CRT), a delay is also caused due to a frame switching timing. Since an X-ray irradiation period of time in a simple X-ray imaging is generally a very short time of about 50 msec, when the delay is caused due to the signal transmission and the frame switching, it may no longer be possible to determine that the X-ray irradiation state is accurately notified.

SUMMARY

An object of the present invention is to provide a radiation control device that controls a radiation imaging system in cooperation with a radiation generation controller, in particular, to provide a radiation control device capable of reliably notifying a radiation irradiation state of a radiation generator, particularly a state during radiation irradiation.

In order to realize at least one of the above objects, a radiation control device reflecting an aspect of the present invention controls a radiation imaging system including a radiation generator and a radiation imager in cooperation with a radiation generation controller, the radiation control device including:

a notifier that provides notification on an irradiation state of radiation in the radiation generator; and a notification controller that controls notification operation of the notifier, in which the notification controller controls a start timing of notification of a state during irradiation indicating that radiation is being emitted on the basis of a signal from the radiation generator or the radiation imager received by the radiation control device prior to a radiation irradiation signal from the radiation generation controller.

BRIEF DESCRIPTION OF DRAWINGS

The advantages and features provided by one or more embodiments of the invention will become more fully understood from the detailed description given hereinbelow and the appended drawings which are given by way of illustration only, and thus are not intended as a definition of the limits of the present invention.

FIG. 1 is a diagram illustrating an X-ray imaging system to which a radiation control device according to an embodiment of the present invention is applied.

DETAILED DESCRIPTION OF EMBODIMENTS

Hereinafter, one or more embodiments of the present invention will be described with reference to the drawings. However, the scope of the invention is not limited to the disclosed embodiments.

Figure 1:
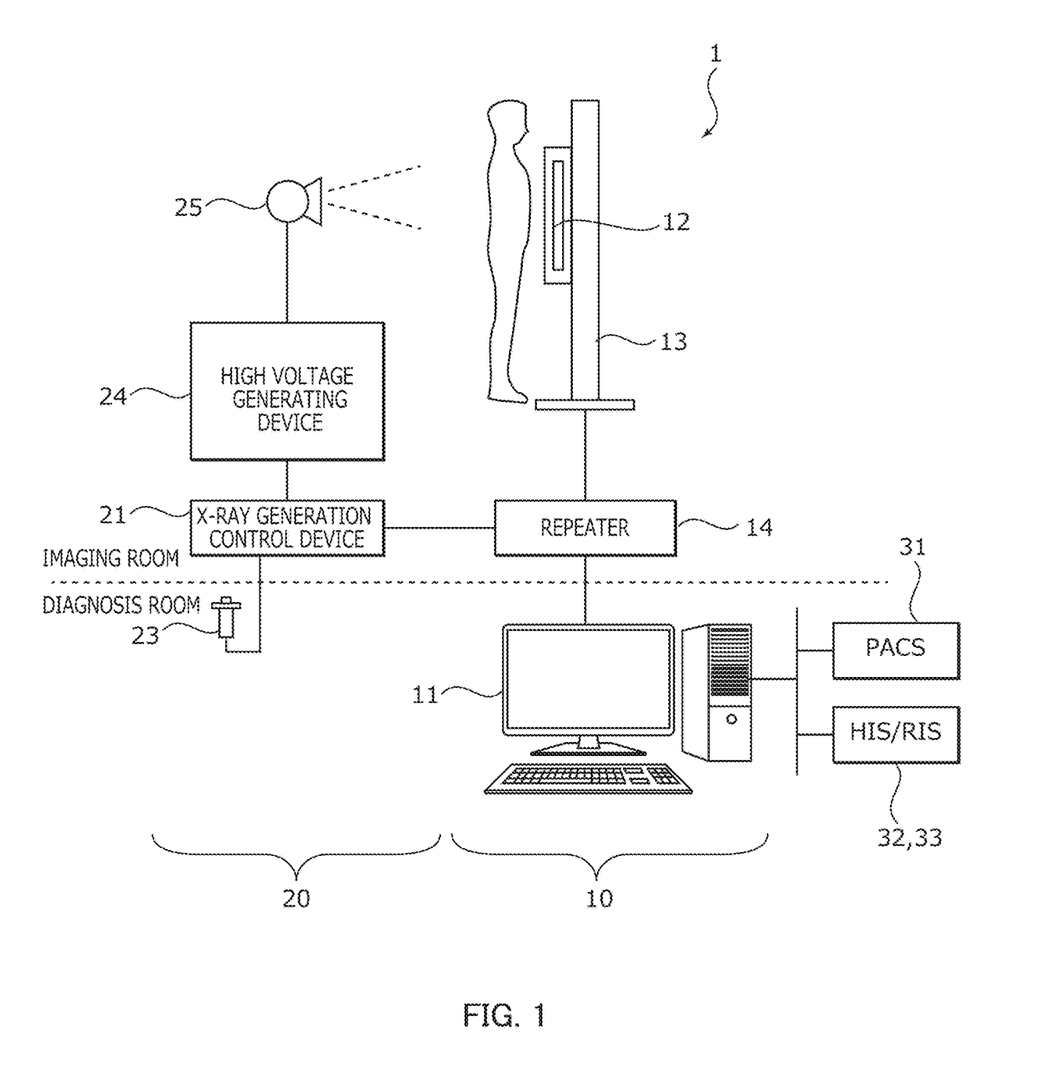

FIG. 1 is a diagram illustrating an X-ray imaging system 1 to which a radiation control device is applied according to an embodiment of the present invention. In the X-ray imaging system 1, the radiation control device according to the present invention is applied to an imaging control device 11. The X-ray imaging system 1 is an integrated imaging system in which a signal or the like is exchanged between an X-ray generating device 20 and an X-ray imaging device 10 and an X-ray imaging is performed while the two devices cooperate with each other.

As illustrated in FIG. 1, the X-ray imaging system 1 includes the X-ray imaging device 10, and the X-ray generating device 20. The X-ray imaging system 1 is connected to, via a communication network, a picture archiving and communication system (PACS) 31, a hospital information system (HIS) 32, and a radiology information system (RIS) 33. In the communication network including the X-ray imaging system 1, the PACS 31, the HIS 32, and the RIS 33, for example, information is transmitted and received in accordance with the digital imaging and communications in medicine (DICOM) standard.

The X-ray imaging device 10 includes the imaging control device 11, the FPD 12, an imaging base 13, a repeater 14, and the like. The X-ray imaging device 10 captures an X-ray image indicating an in-vivo state by visualizing the X-ray having passed through an imaging target portion such as a chest region and an abdomen, for example.

The FPD 12 is an imaging device that detects the X-ray emitted from an X-ray tube device 25 and transmitted through a subject, and outputs X-ray image data. For example, the FPD 12 is attached to the imaging base 13, and communicably connected to the imaging control device 11 by wired communication via the imaging base 13 and the repeater 14. The FPD 12 may be connected to the imaging control device 11 by wireless communication. When the FPD 12 has a wireless communication function, the FPD 12 can be used by, instead of being attached to the dedicated imaging base 13, being placed on a bed on which the subject lies on his/her back or being held by the subject himself/herself.

The FPD 12 includes, for example, a scintillator that converts an incident X-ray into light, a photo diode (PD) disposed in a matrix corresponding to a pixel, and a thin film transistor (TFT) switch disposed corresponding to each PD (all not illustrated). The incident X-ray is converted into light by the scintillator, made incident into the PD, and accumulated as electric charges for each pixel. After flowing out through the TFT switch and a signal line, the electric charges accumulated in the PD is amplified, subject to an A/D conversion, and output to the imaging control device 11 as X-ray image data. The FPD 12 may be of the above-described indirect conversion type, or may be of a direct conversion type that directly converts an X-ray into an electric signal.

The imaging base 13 detachably holds the FPD 12 in such a manner that an X-ray incident surface of the FPD 12 faces the X-ray tube device 25. In FIG. 1, an imaging base for a standing position that captures the subject in a standing posture is illustrated as an exemplary imaging base 13. The imaging base 13 may be an imaging base for a lying position that captures the subject in a lying posture. For example, the imaging base 13 is communicably connected to the imaging control device 11 by wired communication via the repeater 14.

The imaging control device 11 controls the X-ray imaging system 1 in cooperation with an X-ray generation control device 21. For example, the imaging control device 11 transmits a detection condition to the FPD 12, and sets the detection condition. The detection condition includes a size of an image to be captured, a frame rate (in a case of a dynamic imaging), and information associated with signal processing executed by the FPD 12 (e.g., gain of an amplifier). The imaging control device 11 controls each operation of the FPD 12, obtains the X-ray image data from the FPD 12, performs a predetermined image processing, and displays the image data on a display unit 113 (see FIG. 2). Details of the imaging control device 11 will be described later.

Moreover, in the present embodiment, the imaging control device 11 has a function as an irradiation console of the X-ray generating device 20. That is, information associated with the X-ray generating device 20 is displayed and input using the display unit 113 and an operation unit 114 of the imaging control device 11 (see FIG. 2).

The X-ray generating device 20 includes the X-ray generation control device 21, an irradiation switch 23, a high voltage generating device 24, and the X-ray tube device 25.

The X-ray tube device 25 is disposed at a position facing the FPD 12 with the subject interposed therebetween. When a high voltage is applied to the X-ray tube device 25 by the high voltage generating device 24, the X-ray tube device 25 generates an X-ray and irradiates the subject with the X-ray. The X-ray tube device 25 includes an X-ray movable diaphragm that adjusts an irradiation field of the X-ray.

The irradiation switch 23 is connected to the X-ray generation control device 21 via a signal cable. The irradiation switch 23 is a switch for providing an instruction on the X-ray irradiation, and includes, for example, a two-stage automatic reset push button switch. When a first stage pressing operation is performed on the irradiation switch 23, a warm-up start signal for starting a warm-up of the X-ray tube device 25 is transmitted to the X-ray generation control device 21. When a second stage pressing operation is performed on the irradiation switch 23, an irradiation start signal for causing the X-ray tube device 25 to start an X-ray irradiation is transmitted to the X-ray generation control device 21.

The X-ray generation control device 21 controls operation of the high voltage generating device 24 and the X-ray tube device 25 on the basis of the irradiation condition from the imaging control device 11 and the control signal (warm-up start signal and irradiation start signal) from the irradiation switch 23. The irradiation condition includes, for example, a plurality of parameters such as a tube voltage, tube current, radiation exposure time, a radiation exposure dose, a setting mode, a focal point size, a phototimer, a collimater size, a filter type, and an imaging posture (standing/lying).

Figure 2:
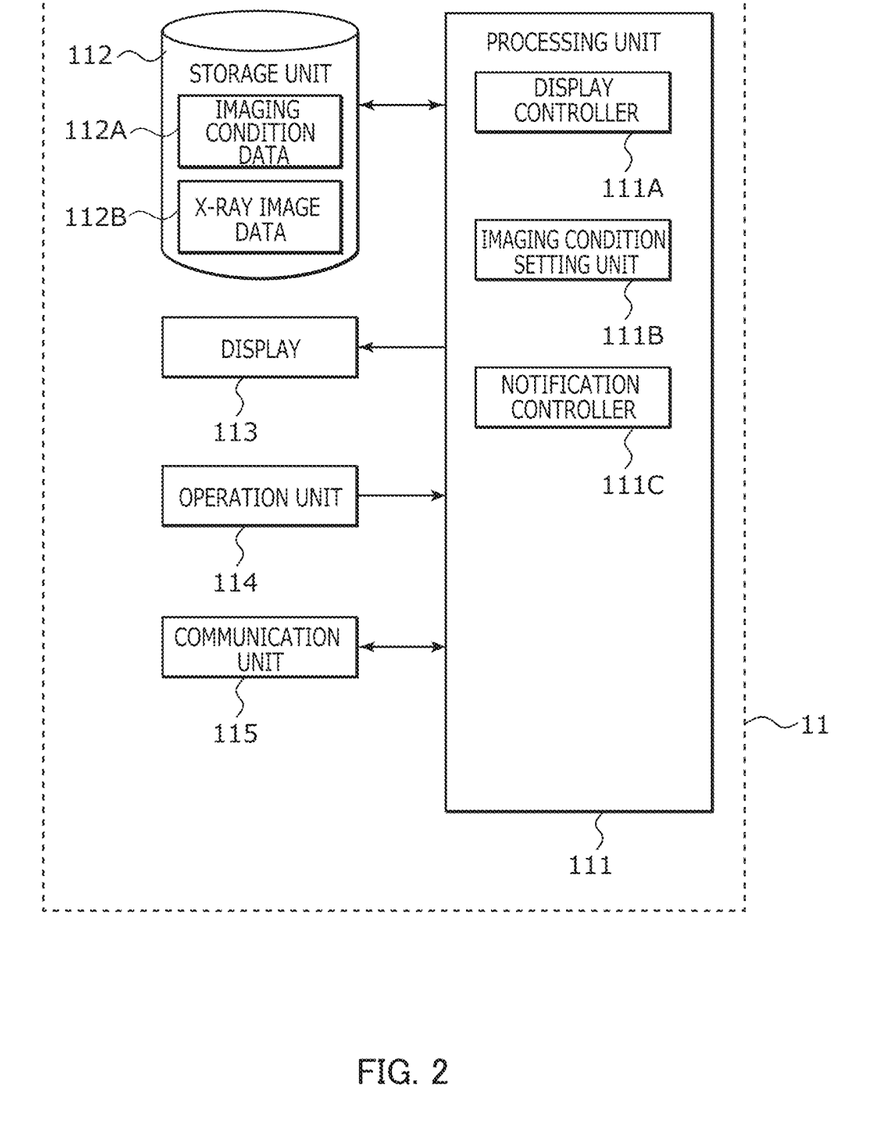
FIG. 2 is a diagram illustrating a configuration of an imaging control device.

The irradiation condition is set using the imaging control device 11. When execution of an examination order is instructed by the imaging control device 11, a predetermined irradiation condition corresponding to the examination order is automatically transmitted to the X-ray generation control device 21 and set. A user can finely adjust the irradiation condition through the operation unit 114 of the imaging control device 11.

FIG. 2 is a diagram illustrating a configuration of the imaging control device 11. As illustrated in FIG. 2, the imaging control device 11 includes a processing unit 111, a storage unit 112, the display unit 113, the operation unit 114, a communication unit 115, and the like.

The processing unit 111 includes a central processing unit (CPU) as an arithmetic/control device, a read only memory (ROM) as a main storage device, a random access memory (RAM), and the like (all not illustrated). A basic program and basic setting data are stored in the ROM. The CPU reads a program corresponding to a processing content from the ROM or the storage unit 112, expands the program in the RAM, and executed the expanded program, thereby centrally controlling operation of the FPD 12 and the like.

The storage unit 112 is an auxiliary storage device such as a hard disk drive (HDD) and a solid state drive (SSD). The storage unit 112 may be a disk drive that reads and writes information by driving an optical disk such as a compact disc (CD) and a digital versatile disc (DVD) and a magneto-optical disk such as a magneto-optical disk (MO). Further, for example, the storage unit 112 may be a memory card such as a USB memory and an SD card.

The storage unit 112 stores various programs to be executed by the processing unit 111, a parameter necessary for the execution of the program, and data such as a processing result. The storage unit 112 stores, for example, imaging condition data 112A and X-ray image data 112B. The imaging condition data 112A includes irradiation condition data in the X-ray generating device 20 and detection condition data in the FPD 12.

The imaging condition is associated with, for example, the imaging content (imaging portion, imaging direction, subject body type, etc.) included in the examination order. When an examination order is selected and the imaging condition is not set to the examination order (e.g., at the time of an initial examination), the imaging condition associated with the imaging content is read out. Here, the initial examination is a first examination performed on the same subject with the same imaging content.

The display unit 113 includes, for example, a flat panel display such as a liquid crystal display and an organic EL display. The display unit 113 displays an examination order content and the captured X-ray image on the basis of a display control signal from the processing unit 111. The examination order includes patient information (e.g., patient ID, patient name, date of birth, and gender) of a patient as a subject, posture information (e.g., posture (standing/lying), and irradiation direction(back/front/side)) at the time of capturing an image, imaging portion information (e.g., chest region), an examination item (e.g., lung ventilation function, and pulmonary blood flow), and an examination history (e.g., imaging condition at the time of previous examination) of the subject.

In the present embodiment, X-ray irradiation information indicating an X-ray irradiation state in the X-ray generating device 20 is displayed on the display unit 113 (see FIGS. 4A to 4D). In other words, the display unit 113 functions as a notification unit according to the present invention.

The operation unit 114 includes a keyboard having a cursor key, a numeric input key, various function keys, and the like, and a pointing device such as a mouse. The operation unit 114 receives an operation signal input by a key operation or a mouse operation, and outputs the operation signal to the processing unit 111. For example, the user can input the imaging condition through the operation unit 114.

Note that the display unit 113 and the operation unit 114 may be integrally configured like a flat panel display provided with a touch panel, for example.

The communication unit 115 is a communication interface such as a network interface card (NIC), a modulator-demodulator (MODEM), a universal serial bus (USB). The processing unit 111 transmits/receives, in accordance with the DICOM standard, various information to/from a device connected to a network such as a wired/wireless LAN via the communication unit 115. A communication interface for short-range wireless communication such as near field communication (NFC) and Bluetooth (registered trademark) may be applied to the communication unit 115.

By executing an imaging program, the processing unit 111 functions as a display control unit 111A, an imaging condition setting unit 111B, and a notification control unit 111C. The imaging program is stored, for example, in the ROM of the processing unit 111.

When the X-ray imaging is performed by the X-ray imaging system 1, the examination order is registered in the imaging control device 11. The registered examination order is displayed on the display unit 113 of the imaging control device 11. The examination order may be input from an external system such as the HIS 32 and the RIS 33, or may be manually input by the user through the operation unit 114. In this case, the examination order is input from an external system such as the HIS 32 and the RIS 33.

When execution of the registered examination order is instructed, the imaging condition included in the examination order is transmitted to the X-ray generation control device 21 and the FPD 12 and set (imaging condition setting unit 111B). At the time of the initial examination, the imaging condition corresponding to the imaging content included in the examination order is read from the storage unit 112 and set. The user can finely adjust the irradiation condition by changing the setting thereof through the operation unit 114. In this case, the irradiation condition having been subject to the setting change is newly transmitted to the X-ray generation control device 21.

When the first stage pressing operation is performed on the irradiation switch 23 by the user, the warm-up (heating of a filament etc.) of the X-ray tube device 25 is started. Along with this, a ready signal (irradiation preparation start signal) indicating that the warm-up has been started is transmitted from the X-ray generation control device 21 to the imaging control device 11. Upon receipt of the ready signal, the imaging control device 11 instructs the FPD 12 to perform imaging preparation (initialization).

When the warm-up of the X-ray tube device 25 is completed, a start signal (irradiation preparation completion signal) indicating that the warm-up has been completed is transmitted from the X-ray generation control device 21 to the imaging control device 11. Further, an OK signal (imaging preparation completion signal) indicating that the imaging preparation has been completed is transmitted from the FPD 12 to the imaging control device 11 and the X-ray generation control device 21.

When the second stage pressing operation is performed on the irradiation switch 23 by the user, the X-ray generation control device 21 transmits an X-ray irradiation signal that provides an instruction on the X-ray irradiation to the high voltage generating device 24 and the imaging control device 11. A high voltage is applied to the X-ray tube device 25 by the high voltage generating device 24, and the X-ray irradiation is started. Here, the second stage pressing operation on the irradiation switch 23 may be performed before accepting the start signal from the X-ray generation control device 21 and the OK signal from the FPD 12. In this case, the X-ray irradiation signal is transmitted from the X-ray generation control device 21 in association with the receipt of the start signal and the OK signal.

In a case where the irradiation period of time is set as in the case of a simple X-ray imaging, the X-ray irradiation is terminated when a predetermined irradiation period of time has elapsed. In a case of the dynamic imaging, the X-ray irradiation is continuously performed during the second stage pressing operation on the irradiation switch 23, and the X-ray irradiation is terminated when the pressing operation on the irradiation switch 23 is released. When the X-ray irradiation is terminated, the X-ray irradiation signal is turned off, and the OK signal, the start signal, and the ready signal are sequentially turned off.

The captured X-ray image is transmitted from the FPD 12 to the imaging control device 11, and stored in the storage unit 112. Various image processing such as an offset correction and a gain correction is applied to the X-ray image data in the imaging control device 11, and the X-ray image data is displayed on the display unit 113 (display control unit 111A).

Figure 3A:
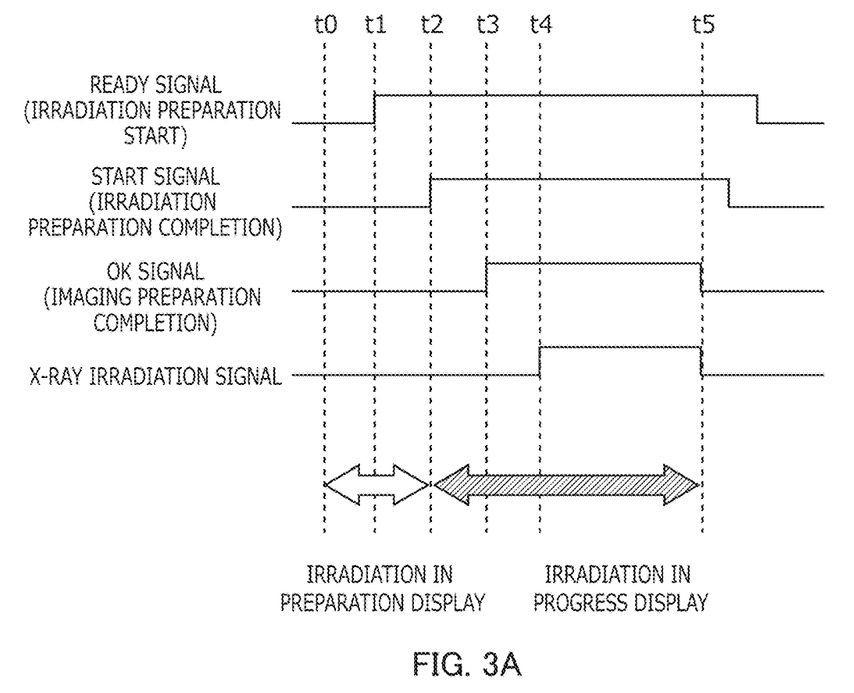
FIGS. 3A and 3B are timing charts illustrating exemplary notification operation performed by a notification control unit.
Figure 3B:
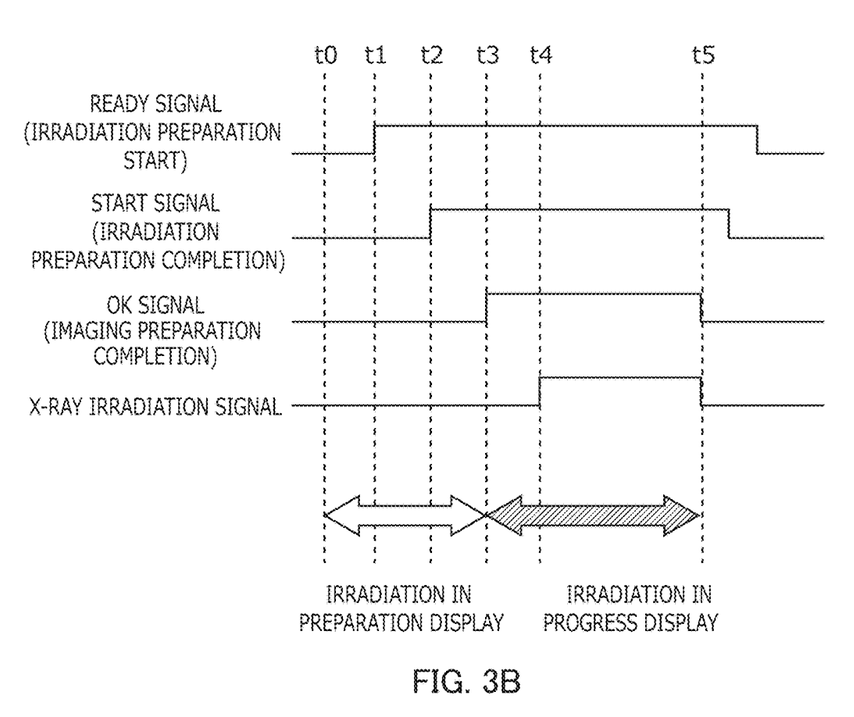

In the imaging control device 11, the notification control unit 111C controls notification operation on the display unit 113. FIGS. 3A and 3B are timing charts illustrating the notification operation performed by the notification control unit 111C. Besides, FIGS. 4A to 4D illustrates an exemplary display of the X-ray irradiation information (mark indicating an irradiation state).

Hereinafter, the X-ray irradiation information indicating an irradiation preparation state is referred to as "irradiation preparation mark", and the X-ray irradiation information indicating a state during irradiation is referred to as "irradiation in progress mark". The irradiation preparation mark is displayed, for example, in a green color, and the irradiation in progress mark is displayed, for example, in an orange color. Further, the first stage pressing operation, the second stage pressing operation, and the release of the pressing operation with respect to the irradiation switch 23 are performed in a series of operations.

FIG. 3A illustrates a case where the display of the irradiation in progress mark is started at a timing t2 at which the start signal is turned on in synchronization with the start signal. In FIG. 3A, the display of the irradiation preparation mark is started at a timing t0 at which the first stage pressing operation is performed on the irradiation switch 23 (see FIG. 4B). Then, at the timing t2 at which the irradiation preparation of the X-ray tube device 25 is completed and the start signal is turned on, the X-ray irradiation information is switched from the irradiation preparation mark to the irradiation in progress mark (see FIG. 4C).

FIG. 3B illustrates a case where the display of the irradiation in progress mark is started at a timing t3 at which the OK signal is turned on in synchronization with the OK signal. In FIG. 3B, the display of the irradiation preparation mark is started at the timing t0 at which the first stage pressing operation is performed on the irradiation switch 23 (see FIG. 4B). Then, at the timing t3 at which the imaging preparation of the FPD 12 is completed and the OK signal is turned on, the X-ray irradiation information is switched from the irradiation preparation mark to the irradiation in progress mark (see FIG. 4C).

Figure 4A:
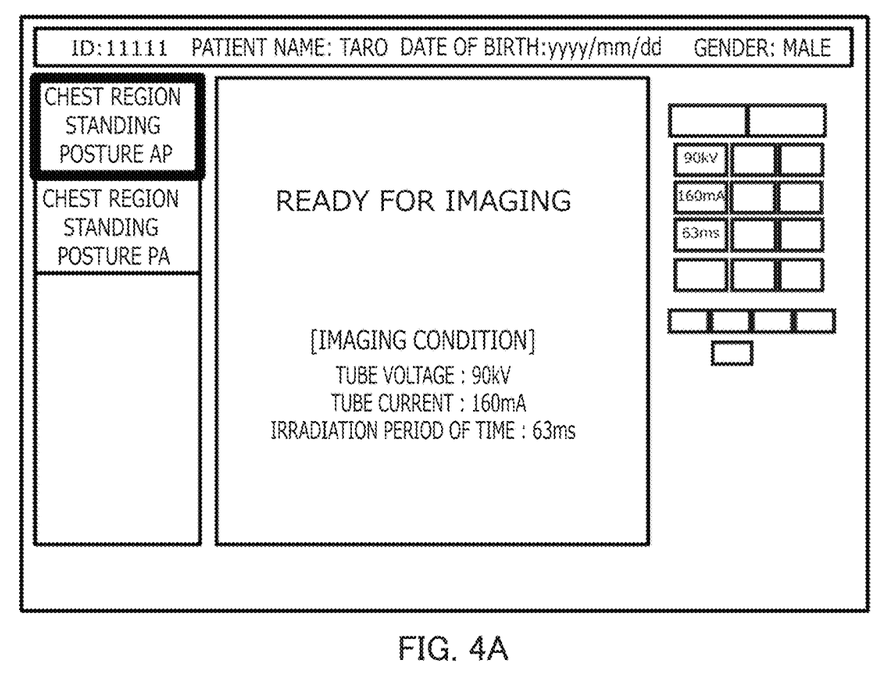
FIGS. 4A to 4D are diagrams illustrating an exemplary display of X-ray irradiation information.
Figure 4B:
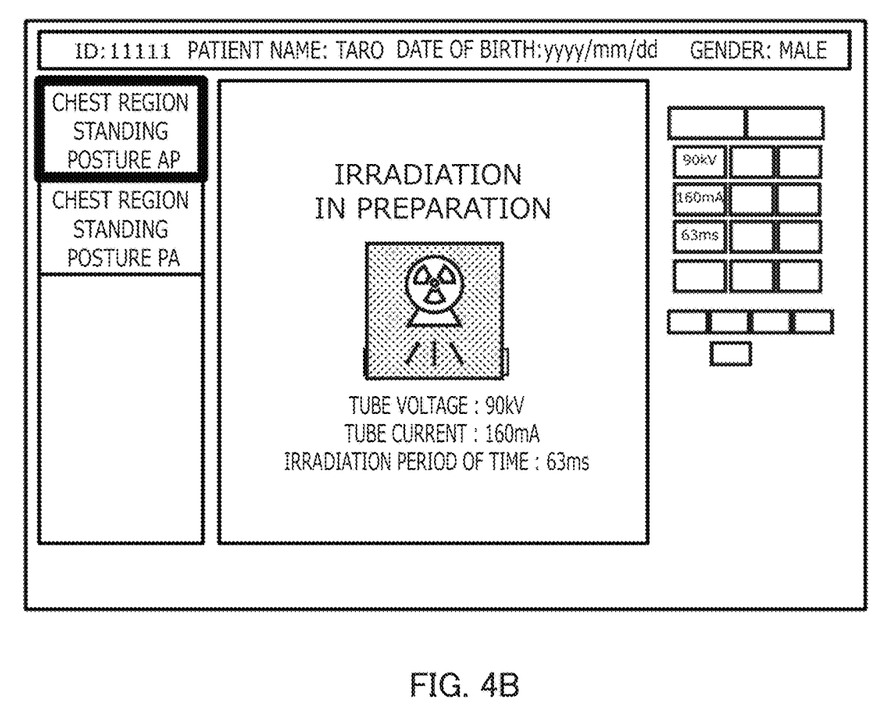
Figure 4C:
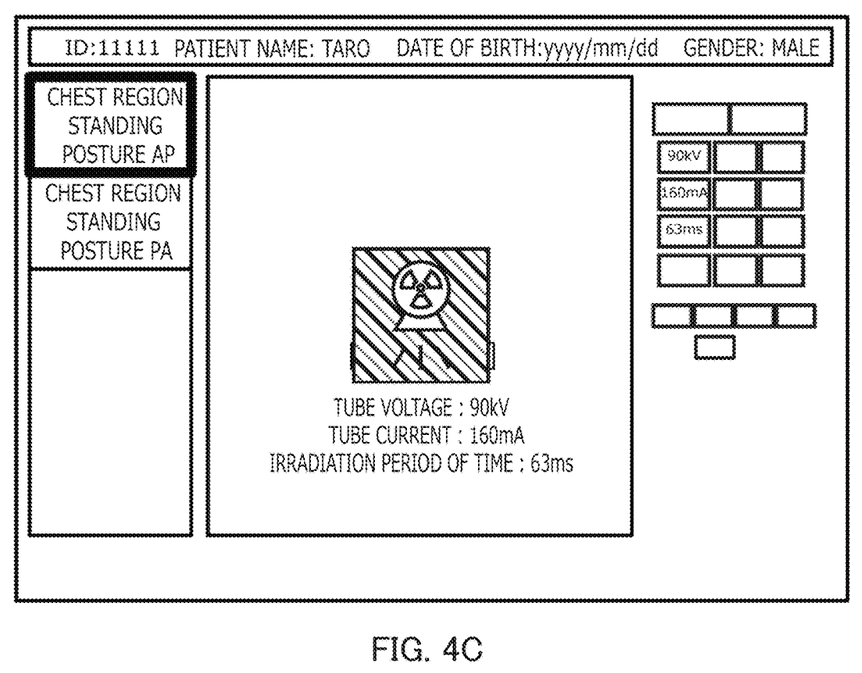
Figure 4D:
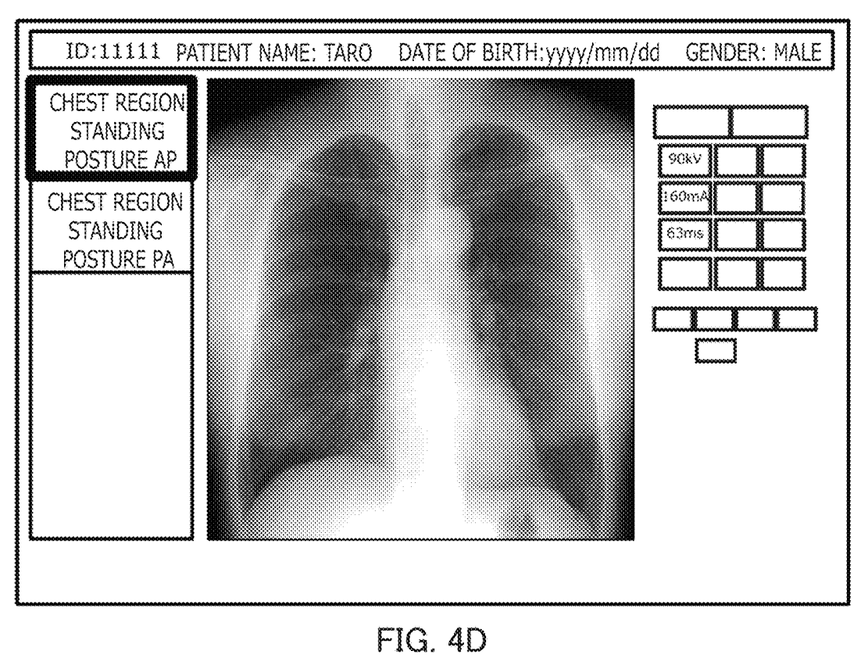

Note that the X-ray irradiation information is not displayed until the first stage pressing operation on the irradiation switch 23 is performed (see FIG. 4A). In addition, the irradiation in progress mark is erased at a timing t5 at which the X-ray irradiation signal is turned off, and the captured X-ray image is displayed (see FIG. 4D).

In either case, the display of the irradiation in progress mark is started before an irradiation start timing t4 instructed by the X-ray irradiation signal. That is, the display of the irradiation in progress mark is controlled in consideration of the signal transmission from the X-ray generation control device 21 and a delay caused by frame switching on the display unit 113. Therefore, the state during X-ray irradiation with respect to the X-ray generating device 20 can be reliably notified.

Here, the notification control unit 111C preferably sets a notification end timing of the irradiation in progress mark in such a manner that the notification period of time (period t2 to t5 in FIG. 3A, and period t3 to t5 in FIG. 3B) of the state during irradiation is equal to or longer than a predetermined period of time. The predetermined period of time is a period of time in which the display of the irradiation in progress mark can be visually recognized, and is preferably 200 msec or more, for example.

For example, when the X-ray irradiation period of time (period t4 to t5 in FIGS. 3A and 3B) is equal to or longer than the predetermined period of time, the display of the state during irradiation is ended at an irradiation end timing (timing t5 in FIGS. 3A and 3B) instructed by the X-ray irradiation signal. Accordingly, the state during irradiation can be reliably recognized without causing the display period of the irradiation in progress mark to differ from the actual irradiation period.

Meanwhile, when the X-ray irradiation period of time (period t4 to t5 in FIGS. 3A and 3B) is shorter than the predetermined period of time, the display of the irradiation in progress mark is ended after the irradiation end timing (timing t5 in FIGS. 3A and 3B). In this case, the irradiation end timing may be set at least to secure the predetermined period of time, and may be or may not be synchronized with the ready signal, the start signal, or the OK signal. In this case, although the display period of the irradiation in progress mark differs from the actual irradiation period (the irradiation in progress mark is displayed even after the actual irradiation is ended), the state during irradiation can be reliably recognized.

As described above, the imaging control device 11 (radiation control device) according to the present embodiment controls the X-ray imaging system 1 (radiation imaging system) including the X-ray generating device 20 (radiation generating device) and the X-ray imaging device 10 (radiation imaging device) in cooperation with the X-ray generation control device 21 (radiation generating control device). The imaging control device 11 includes the display unit 113 (notification unit) that displays the X-ray irradiation state in the X-ray generating device 20, and the notification control unit 111C that controls the notification operation on the display unit 113. The notification control unit 111C controls a notification start timing of the state during irradiation indicating that the X-ray is being emitted on the basis of the signal from the X-ray generating device 20 or the X-ray imaging device 10 received by the imaging control device 11 prior to the X-ray irradiation signal from the X-ray generation control device 21.

With the use of the imaging control device 11, the notification of the state during irradiation is started before the irradiation start timing instructed by the X-ray irradiation signal from the X-ray generating device 20, whereby the X-ray irradiation state of the X-ray generating device 20, particularly the state during the X-ray irradiation can be reliably notified. Therefore, the imaging control device 11 satisfies the safety requirement stipulated by the General Requirements for High-voltage Generators of Medical X-ray Apparatus.

Although the invention made by the present inventor has been concretely described on the basis of the embodiment above, the present invention is not limited to the above-described embodiment, and may be modified without departing from the gist of the present invention.

For example, although the display unit 113 functions as the notification unit of the present invention in the embodiment, an audio output part that provides notification on the state during irradiation using a sound (e.g., buzzer sound) may function as the notification unit.

Further, for example, the timing at which the display of the state during irradiation is started may be at least before the irradiation start timing instructed by the X-ray irradiation signal from the X-ray generating device 20, and may be the timing at which the ready signal is turned on.

Although the case where the present invention is applied to a stationary X-ray imaging system 1 placed in an imaging room in a hospital has been descried in the embodiment, the present invention may be applied to a mobile X-ray imaging system installed on a visiting car.

Although the present invention is implemented by the processing unit 111 (computer) functioning as the notification control unit 111C in the embodiment, this function may be implemented by an electronic circuit such as a digital signal processor (DSP), an application specific integrated circuit (ASIC), and a programmable logic device (PLD).

Further, the present invention may be applied to, not limited to the X-ray imaging system, an imaging system using other radiations such as a γ-ray.

Although embodiments of the present invention have been described and illustrated in detail, it is clearly understood that the same is by way of illustration and example only and not limitation, the scope of the present invention should be interpreted by terms of the appended claims.

What is claimed is:

1. A radiation control device that controls a radiation imaging system including a radiation generator and a radiation imager in cooperation with a radiation generation controller, the radiation control device comprising:

a notification unit that provides notification on an irradiation state of radiation in the radiation generator; and
a notification controller that controls notification operation of the notification unit, wherein
the notification controller controls a start timing of notification of a state during irradiation indicating that radiation is being emitted on the basis of a signal from the radiation generator or the radiation imager received by the radiation control device prior to a radiation irradiation signal from the radiation generation controller.

2. The radiation control device according to claim 1, wherein
the notification controller starts the notification of the state during irradiation in synchronization with an irradiation preparation completion signal indicating that preparation for irradiation from the radiation generator has been completed.

3. The radiation control device according to claim 1, wherein
the notification controller starts the notification of the state during irradiation in synchronization with an imaging preparation completion signal from an imager which captures a radiation image by detecting radiation having passed through a subject, the imaging preparation completion signal indicating that preparation for imaging has been completed.

4. The radiation control device according to claim 1, wherein
the notification controller sets an end timing of the notification of the state during irradiation in such a manner that a notification period of time of the state during irradiation is equal to or longer than a predetermined period of time.

5. The radiation control device according to claim 4, wherein
the notification controller terminates the notification of the state during irradiation at an irradiation end timing instructed by the radiation irradiation signal when a radiation irradiation period of time is equal to or longer than a predetermined period of time, and
the notification controller terminates the notification of the state during irradiation later than the irradiation end timing when the irradiation period of time is shorter than the predetermined period of time.

6. The radiation control device according to claim 1, wherein
the notification unit includes a display that visually provides notification on the state during irradiation, and/or an audio outputter that provides notification on the state during irradiation using a sound.

* * * * *